United States Patent [19]

Young

[11] Patent Number: 4,497,970

[45] Date of Patent: Feb. 5, 1985

[54] AROMATICS PRODUCTION

[75] Inventor: Dennis Young, Staines, England

[73] Assignee: The British Petroleum Company p.l.c., London, England

[21] Appl. No.: 483,102

[22] Filed: Apr. 8, 1983

[30] Foreign Application Priority Data

Apr. 29, 1982 [GB] United Kingdom ............... 8212526

[51] Int. Cl.$^3$ ........................... C07C 2/00; C07C 5/32
[52] U.S. Cl. ................................... 585/417; 585/415; 585/419; 585/431
[58] Field of Search .............. 585/417, 415, 419, 431; 252/455 Z

[56] References Cited

U.S. PATENT DOCUMENTS

| 2,255,421 | 9/1941 | Groll et al. | 423/531 |
| 3,760,024 | 9/1973 | Cattanach | 585/417 |
| 3,775,501 | 11/1973 | Kaeding et al. | 585/417 |
| 3,894,104 | 7/1975 | Chang et al. | 585/417 |
| 3,899,544 | 8/1975 | Chang et al. | 585/417 |
| 4,304,657 | 12/1981 | Miller | 585/415 |
| 4,347,395 | 8/1982 | Chu et al. | 585/419 |
| 4,350,835 | 9/1982 | Chester et al. | 585/415 |

OTHER PUBLICATIONS

Richardson et al., "General College Chemistry," Henry Holt and Company, New York, p. 326.
Arther et al., "Chemistry Dictionary," 6th Edition, Reinhold Publishing Company, New York, pp. 589, 839, 1094.

Primary Examiner—Delbert E. Gantz
Assistant Examiner—Chung K. Pak
Attorney, Agent, or Firm—Brooks, Haidt, Haffner & Delahunty

[57] ABSTRACT

This invention relates to a process for converting a feedstock comprising aliphatic or alicyclic hydrocarbons into aromatic hydrocarbons by bringing into contact in a fluid phase a mixture of the feedstock and an oxidizing agent other than molecular oxygen or a gas containing molecular oxygen into contact with a solid acidic catalyst having Brönsted acid sites. The process is particularly suitable for converting methane, ethane and/or ethylene into aromatics. The solid acidic catalyst with Brönsted acid sites may be an aluminosilicate zeolite with a silica to alumina ratio greater than 12:1. The oxidizing agents other than molecular oxygen or a gas containing molecular oxygen may be selected from nitrous oxide, sulphur trioxide, hydrogen peroxide, ozone, nitric oxide, carbon dioxide and nitrogen oxyfluoride. The process yields high octane value aromatics even from methane at relatively low conversion temperatures.

9 Claims, No Drawings

AROMATICS PRODUCTION

The present invention relates to a process for the production of aromatic hydrocarbons from aliphatic and alicyclic hydrocarbons, in particular from methane and ethane.

Hitherto aromatic hydrocarbons have been produced from lower aliphatic hydrocarbons by the so called dehydrocyclodimerisation process. Such processes are claimed and described for instance in our published British Patent Specification Nos. 1499199, 1507549, 1507778, 1496379, 1533169, 1561590, 1537780 and in our published European Patent Application Nos. 0024147 and 0024930. In these the hydrocarbon reactant is brought into contact with a catalyst such as a gallium compound optionally on a support, eg a zeolite at temperatures above 400° C. and the aromatic hydrocarbons formed thereby recovered.

It has also been known to produce aromatic hydrocarbons by an oxidative dehydrogenation process in which the aliphatic saturated or unsaturated hydrocarbon is brought into contact with a catalyst at elevated temperature in the presence of oxygen or an oxygen containing gas eg air. Such processes are disclosed for example in U.S. Pat. Nos. 3,775,501, 3,786,109 and 3,168,584. However, in all these processes it has been necessary to use a feed containing hydrocarbons or mixtures of hydrocarbons taken from ethylene and hydrocarbons containing at least three carbon atoms.

It has now been found that hydrocarbon feedstock, including those containing only 1 or 2 carbon atoms such as methane and ethane, can be converted to aromatic hydrocarbons by a suitable choice of catalyst and reaction conditions.

Accordingly, the present invention is a process for converting a feedstock comprising aliphatic and/or alicyclic hydrocarbons into aromatic hydrocarbons by bringing a mixture in a fluid phase of said feedstock and an oxidising agent other than molecular oxygen or a gas containing molecular oxygen into contact with a solid acidic catalyst having a Brönsted acid sites.

The hydrocarbon feedstock is suitably a $C_1$-$C_6$ aliphatic hydrocarbon or, where appropriate, an alicyclic hydrocarbon. The process is particularly suited to feedstock comprising methane, ethane and/or ethylene.

Examples of oxidising agents other than molecular oxygen or a gas containing molecular oxygen are nitrous oxide, sulphur trioxide, hydrogen peroxide, ozone, nitric oxide, carbon dioxide and nitrogen oxyfluoride. Nitrous oxide and sulphur trioxide are preferred. The oxidising agents may be used as such in the gaseous phase or in an appropriate fluid medium. It is to be noted that if molecular oxygen or gases containing molecular oxygen are used, they tend to produce deep oxidation products such as carbon oxides and water under the conditions of the present invention, especially when $C_1$ or $C_2$ hydrocarbons are used as feedstock.

By "molecular oxygen" is meant here and throughout the specification the diatomic oxygen molecule $O_2$ but does not include gases such as ozone ($O_3$).

The solid acidic catalyst with Brönsted acid sites is suitably a zeolite, preferably an aluminosilicate zeolite with a silica to alumina ratio greater than 12:1. Zeolites classified as the MFI and MEL types in the book by Meier, W. M. and Olson, D. H. entitled "Atlas of Zeolite Structure Types", published by the Structure Commission of the International Zeolite Association, and distributed by Polycrystal Book Service, Pittsburgh, Pa. USA, are particularly preferred. Specific examples of the MFI type of zeolites are claimed and described in our published European Patent Application Nos. 0002899 and 0002900.

The zeolites of the type referred to above when used as catalysts may optionally contain a further component or components to assist the aromatisation reaction. Such further components may be selected from gallium compounds and a compound of a Group VIII metal according to the Periodic Table due to Mendeleef. The compounds are preferably the oxides of the metals. The further component may be incorporated in the zeolite by ion exchange, impregnation or simple physical mixing. Such techniques of incorporating the further component in the zeolite will be well known to those skilled in the art. It is to be noted that the further component(s) referred to above do not include metal oxide(s) which have a strong oxidising function.

The reaction is carried out in the fluid phase ie a gas or liquid phase in contact with the solid catalyst. The reaction temperatures that may be used vary over a moderately wide range eg from 10° C. to 600° C., preferably from 350° C. to 500° C.

The reaction may be carried out at atmospheric or superatmospheric pressures. The reaction pressure used is suitably between 0.1 and 5 MPa preferably between 0.1 and 1 MPa.

In carrying out the reaction the relative proportion of the hydrocarbon feedstock to the oxidising agent by volume is suitably between 1:1 and 10:1, preferably between 1:1 and 4:1.

In carrying out the process of the present invention, it will be beneficial periodically to restore the activity of the solid acidic catalyst (which inevitably loses some activity in use) by heating it in an atmosphere of a gas containing oxygen or nitrous oxide but in the absence of the hydrocarbon reactant at temperatures from 500°-600° C.

The products of the reactions are rich in aromatics and can either be used as a gasoline blending component (because they have a high octane value) or as a petrochemical feedstock.

The process of the present invention has an advantage over prior processes in that all by-product hydrocarbons such as methane hitherto considered non-desirable can be recycled to extinction to produce aromatics in a single stage. The process is also capable of operating at relatively lower temperatures than used hitherto for aromatisation reactions (especially of light hydrocarbons).

The process of the present invention is further illustrated with reference to the following examples.

EXAMPLES 1-3

A. Catalyst Preparation (a) Sodium hydroxide (10.1 g) and sodium aluminate (25.0 g) were dissolved in deionised water (500 g). Diethanolamine (220 g), tetra-ethyl ammonium hydroxide (55 g of a 25% aqueous solution), and disodium hydrogen orthophosphate (40 g) were added and the resultant solution warmed to 55° C. A solution of 'Ludox AS 40' colloidal silica (Registered Trade Mark, 840 g) and water (1000 g), was added over one hour with rapid agitation. The mixture was stirred for a further 0.5 hour, then left for 1 hour before charging to a 3 liter bomb and heating in a static autoclave at approximately 180° C.

for 6 days. The solid zeolite product was then separated from the mother liquor by filtration.

The zeolite was washed first in water, then in nitric acid solution (10% w/w) and then again in water. The zeolite was then dried under vacuum for 16 hours at 100° C.

The dried zeolite was calcined by heating to 550° C. over 4 hours and holding at that temperature for 18 hours.

The calcined zeolite was then refluxed in 1.75 liter of nitric acid (10% w/w) for 4.25 hours and then water washed.

The acid refluxed zeolite was refluxed for 4 hours in 1.5 liter of 0.71 molar ammonium nitrate solution, then water washed and dried under vacuum at 100° C. for 16 hours.

The ammonium exchanged zeolite was recalcined by raising the temperature to 600° C. over 2 hours and holding for 21 hours to produce the H-zeolite form which had the Brönsted acid sites intact.

(b) Sodium hydroxide (10.0 g) and sodium aluminate (28.0 g) were dissolved in deionised water (350 g) by warming and stirring for 10 minutes. The solution was then filtered and placed in a 3-liter flask. Diethanolamine (262.0 g) was melted and added to this solution and the whole stirred for 10 minutes with the mixture at 40° C. 'Ludox AS 40' colloidal silica (Registered Trade Mark, 714 g) was then diluted with deionised water (500 g) and then slowly added to the mixture in the flask, over a period of 1 hour, and the mixture, which gradually thickened, stirred continuously. Stirring was continued for a further 0.5 hour. The mixture was charged to a 3-liter rocking autoclave which was agitated for 4 hours while the temperature was raised to 175° C. The autoclave was then left static at this temperature for 7 days. Thereafter the autoclave was opened and the white crystalline zeolite which had formed was separated from the mother liquor by decantation.

The crystalline zeolite was then washed thoroughly first with deionised water and then with nitric acid solution (10% w/w). Thereafter the treated zeolite was washed thoroughly with deionised water to remove any traces of acid. This was then dried in a vacuum oven at 100° C. for 16 hours.

The dried zeolite was then calcined in an oven by raising the temperature to 500° C. over 4 hours and holding at that temperature for 60 hours.

The calcined zeolite was then refluxed in 1.6 liter of nitric acid (10% w/w) for 2.5 hours and then water washed and dried in a vacuum oven as before.

The acid washed zeolite was then subjected to ammonium exchange by refluxing in 1.5 liter of 0.67 molar ammonium nitrate solution for 4 hours. It was then water washed and dried as previously to give the ammonium exchanged zeolite.

The ammonium exchanged zeolite was recalcined by raising the temperature to 500° C. and maintained at that temperature for 16 hours to give the H-zeolite form.

The H-zeolite form was placed in 1.65 liter of a solution containing 0.065 moles of gallium nitrate and refluxed for 4 hours. The gallium loaded material was then water washed and dried in a vacuum oven as before.

Gallium loaded zeolite (200 g) was mixed with 'Ludox AS 40' (Registered Trade Mark, containing 40% $SiO_2$) (213 g) and the resulting slurry was dried in a vacuum oven as previously described. The dried product was then broken and sieved to pass 12-30 mesh BSS.

The zeolite so-produced had the majority of its Brönsted acid sites intact.

B. Aromatisation Reaction 5 ml samples of each of the catalysts prepared according to A(a) and A(b) above were loaded into separate reactors. Mixtures of a hydrocarbon feedstock and an oxidising agent (as shown in the Table below) in the gaseous phase were passed into each of the reactors over the loaded catalyst therein at 1 bar pressure. The respective conditions used and the products formed are shown in the Table below.

COMPARATIVE TEST 1 (Not according to the invention)

(a) Catalyst Preparation

The catalyst, ie H-zeolite form, prepared under paragraph A(a) of Examples 1-3 above was treated as follows to remove the Brönsted acid sites: 20 g of this A(a) catalyst was added to a solution of 2 molar sodium nitrate (500 mls). The pH was adjusted to 10 with sodium hydroxide, and then the mixture was stirred under reflux, with periodic readjustment of the pH to 10, until no further reduction in pH occurred. This ensured neutralisation of the Brönsted acid sites. The sodium-zeolite thus obtained was filtered and throughly washed with deionised water and then dried in an oven at 100° C. for 16 hours. The resultant catalyst was substantially free from Brönsted acid sites.

(b) Aromatisation Reaction 5 ml of the zeolite catalyst free from Brönsted acid sites prepared in Comparative Test 1(a) above was loaded into a reactor. A mixture of a hydrocarbon feedstock and an oxidising agent was passed over the loaded catalyst in the gaseous phase therein at 1 bar pressure. The reaction conditions used and the results achieved are also shown in the Table below.

COMPARATIVE TEST 2 (Not according to the invention)

Methane was passed over the H-zeolite form catalyst from Examples 1-3 A(a) above under the same aromatisation conditions as in paragraph B of those Examples, but in the absence of any oxidising agent. The results of this test are also shown in the Table below.

TABLE

| Example | 1 | 2 | 3 | Comp Test 1 | Comp Test 2 |
|---|---|---|---|---|---|
| Catalyst | A(a) | A(a) | A(b) | Na—zeolite | A(a) |
| Hydrocarbon Feed (GHSV)* | $CH_4$(120) | $CH_4$(480) | $C_2H_6$(100) | $CH_4$(120) | $CH_4$(240) |
| Oxidant Feed (GHSV) | $N_2O$(120) | $N_2O$(120) | $N_2O$(100) | $N_2O$(120) | — |
| Temp °C. | 450 | 450 | 450 | 450 | 450 |
| Run Duration (mins) | 315 | 150 | 120 | 165 | 120 |
| Conversion of hydrocarbon feed (%) | 39 | 11 | 62.4 | 5 | 0 |
| Molar yields** (%) of hydrocarbons other than the feed | 8.1 | 2.3 | 14.0 | 0.02 | 0 |
| Hydrocarbon Distribution (wt %) | | | | | |

TABLE-continued

| Example | | 1 | 2 | 3 | Comp Test 1 | Comp Test 2 |
|---|---|---|---|---|---|---|
| Aromatics | $C_1$ | — | — | 5.6 | | |
| | $C_2$ | 5.9 | 2.7 | — | | |
| | $C_3-C_5$ | 3.3 | 1.0 | 15.6 | | |
| | $C_6$ | 3.0 | 3.8 | 37.4 | | |
| | $C_7$ | 9.1 | 13.8 | 34.3 | | |
| | $C_8$ | 25.2 | 29.9 | 11.1 | | |
| | $C_9$ | 16.0   90.8 | 10.8   96.3 | 1.4 | 82.8 | |
| | $C_{10}$ | 6.3 | 9.0 | | | |
| | $C_{11}$ | 16.1 | 16.2 | 0.2 | | |
| $C_{12}$ | | 13.8 | 12.4 | — | | |
| $C_{13}$ | | 1.3 | 0.4 | — | | |

*GHSV = $\dfrac{\text{Individual gas volume flow rate at stp (mls hr}^{-1})}{\text{Catalyst Volume (mls)}}$

**Molar Yield = $\dfrac{100 \times (\text{Number of moles of feed converted to products})}{\text{Number moles of feed passed}}$ The results in the Table above clearly show that when the Brönsted acid sites of the catalyst are removed there is essentially no hydrocarbon oligomerisation, therefore acidity is essential to the reaction. They also show that removal of the oxidising agent also results in a marked reduction in conversion in the case of methane.

I claim:

1. A process for converting a feedstock consisting essentially of methane or ethane into aromatic hydrocarbons by bringing at a temperature of from about 350° to 500° C. a mixture in a fluid phase of said feedstock and an oxidizing agent selected from the group consisting of nitrous oxide, sulfur trioxide, hydrogen peroxide, ozone, nitric oxide, and nitrogen oxyfluoride into contact with a solid acidic catalyst having Bronsted acid sites.

2. A process according to claim 1 wherein the solid acidic catalyst with Brönsted acid sites is an aluminosilicate zeolite with a silica to alumina ratio greater than 12:1.

3. A process according to claim 2 wherein the zeolite contains a further component or components selected from a gallium compound and a compound of a Group VIII metal according to the Periodic Table due to Mendeleef.

4. A process according to claim 3 wherein the compounds are the oxides of the metals.

5. A process according to claim 1 wherein the reaction is carried out at a pressure of between 1 and 50 bar.

6. A process according to claim 1, wherein the relative proportions of the hydrocarbon feedstock to the oxidising agent by volume is between 1:1 and 10:1.

7. A process according to claim 1 wherein the feedstock consists essentially of methane.

8. A process according to claim 1 wherein the feedstock consists essentially of ethane.

9. A process according to claim 7 or 8 wherein the oxidizing agent is selected from the group consisting of nitrous oxide and sulfur trioxide.

* * * * *

UNITED STATES PATENT AND TRADEMARK OFFICE
CERTIFICATE OF CORRECTION

PATENT NO. : 4,497,970
DATED : February 5, 1985
INVENTOR(S) : DENNIS YOUNG

It is certified that error appears in the above-identified patent and that said Letters Patent is hereby corrected as shown below:

In the Table between columns 5 and 6, the bottom 2 lines have been misaligned and should be moved to the right as follows:

Each of $C_{12}$ and $C_{13}$ should be immediately under $C_{11}$ in the column of aromatics Each of 13.8 and 1.3 should be immediately under 16.1 in the column headed Example 1

Each of 12.4 and 0.4 should be immediately under 16.2 in the column headed Example 2

Each of - and - should be immediately under 0.2 in the column headed Example 3

Signed and Sealed this

Sixth Day of August 1985

[SEAL]

Attest:

DONALD J. QUIGG

*Attesting Officer*     Acting Commissioner of Patents and Trademarks